United States Patent [19]

Cornell et al.

[11] Patent Number: 5,120,779

[45] Date of Patent: * Jun. 9, 1992

[54] TIRE SIDEWALL

[75] Inventors: Robert J. Cornell, Naugatuck; Edward L. Wheeler, Watertown; Russell A. Mazzeo, Waterbury; Sung W. Hong, Cheshire, all of Conn.

[73] Assignee: Uniroyal Chemical Company, Inc., Middlebury, Conn.

[*] Notice: The portion of the term of this patent subsequent to Dec. 27, 2005 has been disclaimed.

[21] Appl. No.: 562,522

[22] Filed: Aug. 3, 1990

Related U.S. Application Data

[60] Division of Ser. No. 163,921, Mar. 4, 1988, Pat. No. 4,946,881, which is a continuation-in-part of Ser. No. 90,298, Aug. 28, 1987, Pat. No. 4,794,135.

[51] Int. Cl.⁵ .......................... C08K 5/34; C08K 5/17
[52] U.S. Cl. ...................... 524/100; 524/186; 524/236; 524/241; 524/254; 524/255; 524/256; 524/258; 524/323; 524/611; 525/331.8; 301/5 R
[58] Field of Search ............... 524/100, 186, 254, 255, 524/256, 258, 236, 241, 323, 611; 525/331.8; 301/5 R

[56] References Cited

U.S. PATENT DOCUMENTS

| 3,179,718 | 4/1965  | Wei et al.        | 525/233 |
| 3,350,449 | 10/1967 | Wheeler et al.    | 564/434 |
| 3,379,676 | 4/1968  | Ashton et al.     | 524/100 |
| 3,419,639 | 4/1968  | Gentile           | 525/233 |
| 3,630,974 | 12/1972 | Ladocsi et al.    | 525/233 |
| 3,706,819 | 12/1972 | Usamoto et al.    | 525/233 |
| 3,830,274 | 8/1974  | Waser, Jr.        | 525/233 |
| 3,915,907 | 10/1975 | Hopper            | 152/524 |
| 3,937,862 | 2/1976  | Dillenschneider   | 152/353 |
| 4,003,420 | 1/1977  | Sandstrom et al.  | 428/409 |
| 4,479,008 | 10/1984 | Batorewicz et al. | 564/433 |
| 4,518,803 | 5/1985  | Batorewicz et al. | 564/410 |
| 4,645,793 | 2/1987  | Von Hellens et al.| 524/510 |
| 4,794,134 | 12/1988 | Wheeler et al.    | 524/100 |
| 4,794,135 | 12/1988 | Wheeler et al.    | 524/100 |
| 4,946,881 | 8/1990  | Cornell et al.    | 524/100 |
| 4,962,142 | 10/1990 | Migdal et al.     | 524/100 |
| 4,972,010 | 11/1990 | Wheeler et al.    | 524/100 |

Primary Examiner—Kriellion S. Morgan
Attorney, Agent, or Firm—Raymond D. Thompson

[57] ABSTRACT

A new class of antiozonant compounds, namely tris(N-alkyl-p-phenylenediamino)-1,3,5-triazine compounds, are incorporated into thermosetting compositions having at least one highly unsaturated rubbery polymer and at least one other elastomer having lesser unsaturation, such as EPDM. Thermosetting compositions are most useful as tire sidewall compositions which may be preferably cured with blends of organic peroxide and sulfur donor accelerators.

20 Claims, No Drawings

TIRE SIDEWALL

CROSS-REFERENCE TO RELATED APPLICATION

This is a division of application Ser. No. 07/163,921 filed Mar. 4,1988, now U.S. Pat. No. 4,946,881 which is a continuation-in-part of application Ser. No. 90,298 filed Aug. 28, 1987, now U.S. Pat. No. 4,794,135.

BACKGROUND OF THE INVENTION

This invention relates to the use of new triazine as antiozonants for thermosetting rubber compositions and their preferred use as sidewall components in tires. More particularly, their use in blends of highly unsaturated rubbers and rubbers with lesser unsaturation, such as EPDM.

It is well known that ozone causes surface cracking of conventional highly unsaturated rubber vulcanizates used in tires when the rubber is placed under strain in an ozone environment. The most severe deterioration occurs when a small number of cracks are formed which grow rapidly into deep, disruptive fissures. These ozone cracks seriously shorten the serviceable life of the tire, especially in the area of the sidewall.

Conventional chemical antiozonants have been developed which retard the formation of the ozone cracks occurring under static and dynamic conditions. Examples of antiozonants in common use include: N-phenyl-N'-(1,3-dimethylbutyl)-p-phenylenediamine; N-phenyl-N'-isopropyl-p-phenylenediamine; N-phenyl-N'-(1,4-dimethylpentyl)-p-phenylenediamine; N-phenyl-N'-(1-methylheptyl)-p-phenylenediamine; N-phenyl-N'-cyclohexyl-p-phenylenediamine; mixed diaryl-p-phenylenediamines; N,N'-diphenyl-p-phenylenediamine; N,N'-di-beta-naphthyl-p-phenylenediamine; N,N'-bis(1,4-dimethylpentyl)-p-phenylenediamine; N,N'-bis(1-ethyl-3-methylpentyl)-p-phenylenediamine; N,N'-bis(1-methylheptyl)-p-phenylenediamine; N-phenyl-N'-p-toluenesulfonyl-p-phenylenediamine and blends of these materials.

The use of these well known paraphenylenediamine materials has improved ozone protection under both static and dynamic conditions, however, even the best of the class just described have a very strong tendency to both stain and discolor. The term "stain" or "staining" is herein used to describe the characteristic of a material to diffuse through a polymeric substrate and discolor the adjacent surface. This diffusion staining is highly objectionable in most light colored rubber articles. In tires, which is the largest application in which the ozone protection is required, the tendency to diffusion staining of the aforementioned paraphenylenediamine materials is objectionable particularly in white sidewall type tires. Even in non-white sidewall type tires, the tendency of the materials to diffuse to the surface of the tire sidewall can be objectionable in that a brown, dull surface is created on the tire sidewall. This is aesthetically objectionable in that it detracts from the general jet black, smooth appearance of a new tire. It is obvious that in a white sidewall tire, the migration of the brown discoloring material to the surface of the white sidewall is highly objectionable and generally difficult to remove during cleaning of the tire surface.

Rubbers with lesser unsaturation have been blended with the highly unsaturated diene based rubber to protect against ozone as disclosed in U.S. Pat. Nos. 3,630,974; 3,706,819; 3,830,274; 3,915,907; 3,937,862 and 4,224,196. These have resulted in improved ozone resistance but reduced other desirable properties, such as adhesion, flex fatigue and others.

An object of this invention is to provide an antiozonant material which is highly effective in protecting the carcass from ozone attack. A further object is to provide ozone protection to an EPDM/diene-type rubber blend and to improve flex fatigue of the tire into which this blend is incorporated. Yet another object is to produce an ozone protection which slowly diffuses and does not produce an objectionable brown bloom on a black or white sidewall.

The novel arylenediamine substituted triazine compounds of the invention have provided exceptional long term ozone protection under static conditions without using wax. An advantage of the substituted triazine compounds is that it produces a substantially non-staining antiozonant of high molecular weight. A further advantage is that it slowly blooms to the surface of the rubber article. A further advantage is that the triazine compounds of the invention provide outstanding dynamic protection without the use of waxes preferably by blending said triazine compounds with other known antiozonants and antioxidants. Another advantage is that the compounds do not tend to increase scorchiness of the compounded rubber stock in which it is used. This improves processing safety over other paraphenylenediamine antiozonants.

BRIEF DESCRIPTION OF THE INVENTION

The object and advantages of the invention may be obtained using the essential ingredient of the invention which is a compound of the general formula:

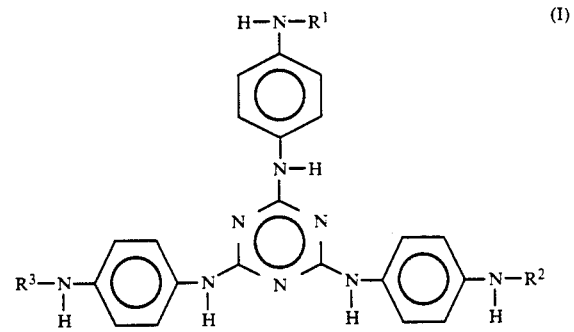

in which $R^1$, $R^2$ and $R^3$ are radicals independently selected from a $C_3-C_{18}$ branched or linear alkyl, or a $C_3-C_{12}$ cycloalkyl or a $C_3-C_{12}$ cycloalkyl substituted with one or more $C_1-C_{12}$ alkyl groups. The compound of structure (I) is incorporated into a thermosetting composition or a tire comprising at least one highly unsaturated rubbery polymer and at least one other elastomer having lesser unsaturation, such as an EPDM, EPR or butyl rubber. The composition may be sulfur cured or preferably cured using a blend of an organic peroxide with sulfur or a sulfur donor accelerator.

DETAILED DESCRIPTION OF THE INVENTION

Referring now to structure (I), the preferred compositions are those in which $R^1$, $R^2$ and $R^3$ are linear or branched $C_3-C_{18}$ alkyl groups. The alkyl groups more preferred are those with a secondary carbon in the alpha position to the nitrogen. In this configuration, the antiozonant activity of the compound is believed to be enhanced. Therefore, the more preferred alkyl groups are branched chains which provide an alkyl substituent which is in accordance with this configuration. The cycloalkyl or $C_1$-$C_{12}$ alkyl substituted cycloalkyls provide such a alpha carbon configuration as well. The structure of formula I which is most preferred at this time are compounds in which $R^1$, $R^2$ and $R^3$ are $C_6$-$C_8$ branched chain alkyl groups. Examples of some preferred chemicals of the present invention are: 2,4,6-tris(N-1,4-dimethylpentyl-p-phenylenediamino)-1,3,-5-triazine: 2,4,6-tris(N-isopropyl-p-phenylenediamino)-1,3,5-triazine; 2,4,6-tris(N-cyclohexyl-p-phenylenediamino)-1,3,5-triazine; 2,4,6-tris(N-sec-butyl-p-phenylenediamino)-1,3,5-triazine; 2,4,6-tris(N-1,3-dimethylbutyl-p-phenylenediamino)-1,3,5-triazine; 2,4,6-tris (N-1-methylheptyl-p-phenylenediamino)-1,3,5-triazine; 2,4,6-tris(N-2,4-di-tert-butylcyclohexyl-p-phenylenediamino)-1,3,5-triazine; 2,4,6-tris(N-2-sec-butylcyclohexyl-p-phenylenediamino)-1,3,5-triazine, 2,4,6-tris(1-methyldecyl-p-phenylenediamino)-1,3,5-triazine. The most preferred material 2,4,6-tris(N-1,4-dimethylpentyl-p-phenylenediamino)-1,3,5-triazine.

The compounds of the invention are most advantageously utilized as antiozonants to protect blends of highly unsaturated polymers such as natural or synthetic elastomers and polymers of lesser unsaturation, such as EPDM or butyl rubber. Representative of the highly unsaturated polymers which may be employed in the practice of this invention are diene elastomers. Such elastomers will typically possess an iodine number of between about 100 and about 400, although highly unsaturated rubbers having a higher or a lower (i.e., of 50-100) iodine number may also be employed. Illustrative of the diene elastomers which may be utilized are polymers based on conjugated dienes such as 1,3-butadiene; 2-methyl-1,3-butadiene; 1,3-pentadiene; 2 chloro-1,3 butadiene, 2,3-dimethyl-1,3-butadiene; and the like, as well as copolymers of such conjugated dienes with monomers such as styrene, alpha-methylstyrene, acrylonitrile, methacrylonitrile, methyl acrylate, ethyl acrylate, methyl methacrylate, ethyl methacrylate, vinyl acetate and the like. Solution polymerized butadiene styrene copolymers and polypentenamers of the type derived from ring opening polymerization of cyclopentene materials, alternately known as transpolypentene, may also be found useful. Preferred highly unsaturated rubbers include natural rubber, cis-polyisoprene, polybutadiene, poly(styrenebutadiene), polychloroprene and poly(acrylonitrilebutadiene). Moreover, mixtures of two or more highly unsaturated rubbers may be employed. Mixtures of the highly unsaturated rubbers with elastomers having lesser unsaturation such as EPDM (ethylene-propylenediene rubber), EPR (ethylene propylene rubber), butyl or halogenated butyl rubbers are most preferred in this invention. These lesser unsaturation elastomers or rubbers have iodine numbers below 100 and preferably between 10 and 100, more preferably between 10 and 50. Typical EPDM polymers have iodine numbers between 20 and 40.

U.S. Pat. No. 3,706,819 broadly discloses the use of EPDM terpolymers with other highly unsaturated rubbers where the EPDM has an ethylene/propylene ratio range of 80/20 to 20/80 and a non-conjugated diene content of 2-20 weight percent.

U.S. Pat. No. 4,645,793 (Von Hellems et al) discloses particularly preferred high molecular weight EPDM polymers of this high molecular weight class that have an ethylene:propylene weight ratio of about 50:50 to about 75:25, preferably from 60-40 to about 75:25 and at least about 6 and preferably at least about 7.5, most preferably at least about 9 and up to about 15 weight percent bound non-conjugated diene based on the total EPDM. Suitable such non-conjugated dienes include straight chain and cyclic dienes such as 1,4-hexadiene, ethylidene norbornene, norbornadiene, methylene norbornene, dicyclopentadiene, 2-methyl norbornadiene, 5-vinyl 2 norbornene and the like. Especially preferred among such dienes is ethylidene norbornene. Preferably, the EPDM has a non-conjugated diene content of 7.5-15 weight percent. Methods for production of such EPDM polymers are well documented in the art. Preferably the amount of EPDM polymer in the elastomeric composition is from 15 to about 50 parts by weight per 100 parts by weight of total elastomers.

For ease and efficiency of mixing the polymers, the high molecular weight EPDM polymer is provided as an oil extended polymer prior to mixing with the other polymers. The EPDM may be oil extended by the well-known procedures of oil extending polymers by adding oil to the polymer solution from the polymerization reactors and recovering the oil extended polymer; the oil is selected from aromatic, naphthenic or paraffinic oils, in amounts from about 50 to about 150 parts by weight of oil per 100 parts by weight of EPDM polymer. Alternatively, the oil can all be separately added to the high molecular weight EPDM polymer during the process of compounding the polymers.

Another EPDM polymer considered useful in this invention is disclosed in U.S. Pat. No. 3,915,907 (Hopper) in which a modified rubbery terpolymer is provided which comprises an admixture of a rubber terpolymer of ethylene, alpha-olefin containing 3-6 carbon atoms and a non-conjugated diene containing 6-12 carbon atoms with an N-chlorothio-sulfonamide of the formula

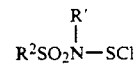

where the mole ratio of said N-chlorothio-sulfonamide to unsaturated sites in said terpolymer is in the range of about 0.06:1 to 1:1, where R' and $R^2$ are selected from the group consisting of alkyl radicals having 1-20 carbon atoms, aralkyl radicals having 7-20 carbon atoms, alkaryl radicals having from 7-20 carbon atoms, and haloaryl radicals having 6-10 carbon atoms and where R" is also selected from radicals having the formula

where $R^3$ and $R^4$ are individually selected from said alkyl, aralkyl and haloaryl radicals where $R^3$ and $R^4$ can be joined together to represent radicals selected from —$CH_2$—, where n is an integer of 4-7, and —($CH_2$)$_2$—O—($CH_2$)—.

Blends of highly unsaturated rubber with both EPDM and halobutyl rubbers are also considered useful in this invention. Such blends are known as noted below but the results may be surprisingly enhanced by the addition of triazine compound (I) of the invention.

U.S. Pat. No. 3,630,974 (Ladocsi et al) discloses a composition which provides a vulcanizate with good dynamic ozone resistance and heat-flex resistance, provided by compounding an amount of halobutyl rubber, i.e. 25–30 weight percent, with high unsaturation rubber and a terpolymer comprised of ethylene, lower 1-alkene and non-conjugated diene, i.e. an EPDM. The EPDM polymer used in the compositions of Ladosci et al comprise 20–80 percent by weight ethylene, 75–15 percent by weight of $C_2$-$C_{10}$ alkene (normally propylene) and no more than 20 percent by weight of the diene, most preferably 0.1–6 mole percent. In the sidewall compositions as a whole, the EPDM polymer represents 15–30 percent by weight.

U.S. Pat. No. 3,830,274 (Waser) discloses an elastomer blend and a pneumatic tire sidewall prepared therefrom which comprise 20–60 percent weight percent of either natural or synthetic cis-1,4-polyisoprene compounded with 20–35 weight percent of EPDM polymer and with from 20–45 weight percent of bromobutyl rubber having specific characteristics. The EPDM component of the invention is defined in preferred terms as having the following constitution: ethylene to propylene ratio of 50:50 to 75:25 based on weight and from 2–20 weight percent units of non-conjugated diene.

In U.S. Pat. No. 4,224,196 (Gursky) there is disclosed a pneumatic tire sidewall composition which comprises a halobutyl rubber, a high unsaturation rubber and an oil extended EPDM polymer. The EPDM polymer component of the disclosed composition is described as comprising ultra high molecular weight polymers which have prior to oil extension a Mooney viscosity in excess of about 100 at 260° F., an ethylene content of between 50 and 75 percent and a diene level of from 3 percent to 12 percent. Napthenic and paraffinic oils, in amounts from 25–150 parts by weight per hundred parts by weight of polymer, are used for EPDM oil extension.

The tire, in accordance with the invention whose sidewalls are formed at least on the outer surface, of one or more blends of elastomers of the diene type and of the ethylene-propylene type is characterized by the fact that the portions of the sidewalls formed of the said blends are vulcanized by means of an organic peroxide and sulfur and/or sulfur donor type accelerators.

The ethylene-propylene elastomer which is of preferred use is an ethylene-propylene-diene terpolymer containing a small portion of a diene selected generally from among ethylidene norbornene, hexadiene-1,4, or, more exceptionally, from among methylene norbornene, dicyclopentadiene and cyclo-octadiene-1,5. It is particularly surprising that it is advantageous to covulcanize with peroxides an ethylene-propylene-diene terpolymer into which a diene has been introduced to facilitate a sulfur vulcanization.

The amount of elastomer of the ethylene-propylene type to be used is between about 15 percent and about 60 percent by weight of the total elastomers, the balance being formed of ordinary highly unsaturated diene-based elastomers. A smaller amount—about 20 percent to about 40 percent by weight constitutes the preferable range—can be used with a terpolymer having a high content of macromolecules of high molecular weight, that is to say a terpolymer having a Mooney plasticity ML (1+8′) of more than about 100 at 100° C. for the non-oil extended base polymer. The best proportion is between about 30 percent and about 45 percent by weight for an ordinary terpolymer containing a relatively large number of macromolecules of relatively low molecular weight, that is to say, having a Mooney plasticity of between about 50 and about 100 at 100° C. The use of an ethylene-propylene copolymer is believed to require a higher proportion for the same effectiveness. However, one maybe able to use such a copolymer possibly mixed with a terpolymer to good advantage.

The curative system employed when blends of highly unsaturated and lesser unsaturation rubbers are utilized is critical to good physical properties. Any conventional sulfur cure system may be employed. A preferred system comprises a sulfur containing cure component selected from sulfur or a sulfur donor compound, at least one sulfur cure accelerator and at least one organic peroxide curative.

The sulfur donor compounds which may be employed in conjunction with or in the alternative to sulfur are well known to those skilled in the art of rubber compounding. Illustrative of such sulfur donor compounds are 2-(4-morpholinyldithio)benzothiazole, tetramethylthiuram disulfide, tetraethylthiuram disulfide, dipentamethylene thiuram hexasulfide, N,N′-caprolactam disulfide and the like.

The sulfur cure accelerators which may be employed include thioureas, such as N,N′-dibutylthiourea, 2-mercaptoimidazoline, tetramethylthiourea and the like; guanidine derivatives, such as N,N′-diphenylguanidine and the like; xanthates, such as zinc dibutylxanthate and the like; dithiocarbamates, such as zinc dimethyldithiocarbamate, zinc diethyldithiocarbamate, zinc dibutyldithiocarbamate, sodium diethyldithiocarbamate, and the like; thiuramsulfides, such as dipentamethylenethiuram disulfide, dipentamethylenethiuram hexasulfide, tetrabutylthiuram monosulfide, tetramethylthiuram monosulfide, tetraethylthiuram monosulfide, tetraethylthiuram disulfide and the like; heterocyclics, such as mercaptobenzimidazole, mercaptobenzthiazole, 2,2′-dibenzothiazyl disulfide, zinc 2-mercaptobenzothiazole and the like; and sulfenamides, such as N-oxydiethylene-2-benzothiazolesulfenamide, N-t-butylbenzothiazylsulfenamide, N-cyclohexyl2-benzothiazylsulfenamide, N,N-diisopropyl-2-benzothiazylsulfenamide and the like. Moreover, mixtures of two or more sulfur cure accelerators may be employed in the curing agent. The preferred accelerators are thiazoles and sulfenamides, with sulfenamides being particularly preferred.

The peroxides which may be employed in this invention have an activation temperature which is below the decomposition temperature of the rubbers employed. Illustrative of such peroxides are benzoyl peroxide, dibenzoyl peroxide, 1,3-bis(t-butylperoxyisopropyl)-benzene, diacetyl peroxide, butyl 4,4-bis(t-butylperoxy)valerate, p-chlorobenzoyl peroxide, cumene hydroperoxide, t-butyl cumyl peroxide, t-butyl perbenzoate, di-t-butyl peroxide, dicumyl peroxide, 2,5-dimethyl-2,5-di-t-butylperoxyhexane, 2,5-dimethyl-2,5-di-t-butyl-peroxyhex-3-yne, 4-methyl-2,2-di-t-butylperoxypentane and the like. Mixtures of two or more peroxides may also be employed. The preferred peroxides are dicumyl peroxide and 2,5-dimethyl-2,5-di-t-butylperoxyhexane.

There are available on the market various packaged products known under their trademarks; mention may be made of:

Dicup 40, manufactured by Hercules Chemical Co., containing 40 percent dicumyl peroxide;

Perkadox Y12, manufactured by Noury van der Lande, containing 40 percent bis(tert.butylperoxyisopropyl) benzene;

Peroximon F40, manufactured by Montecatini Edison, S.p.A., containing 40 percent bis(tert.-butylperoxy) diisopropyl benzene;

Trigonox, manufactured by Noury van der Lande, containing 40 percent 1,1-di-tert-butyl-peroxy 3,3,5-trimethyl cyclohexane;

Varox, manufactured by R. T. Vanderbilt Co., containing 50 percent 2,5-dimethyl-2,4-bis(tert.-butyl peroxy) hexane; and Luperko, manufactured by Wallace & Tiernan, Inc., containing 45 percent 2,5-dimethyl-2,5-bis(tert.-butyl peroxy)hexyne-3.

Typically, between about 0.5 and about 200, preferably between about 5 and about 150, and most preferably between about 6 and about 14, gram atoms of sulfur per mole of peroxide are present in said curing agent.

The sulfur cure accelerator is generally present in amounts of between about 0.1 part and about 5 parts per 100 parts of rubber, with preferably between about 0.3 part and about 3.0 parts of accelerator per 100 parts of rubber being present. Most preferably, between about 0.3 part and about 1.0 part of accelerator per 100 parts of rubber are employed.

Generally, between about 0.2 and about 5, preferably between about 0.5 and about 3, and more preferably between about 0.5 and about 1.5 parts of sulfur per hundred parts by weight of rubber are employed. Employing the ratios of sulfur to peroxide stated above, one skilled in the art can easily calculate the corresponding amount of the particular peroxide which is to be employed. Generally, however, the amount of organic peroxide to be used is from about 0.3 to about 10 parts by weight per 100 parts by weight of elastomers, and preferably from about 0.3 to about 5 parts by weight. These ranges are based on 100% active product and are adjusted for products with less active ingredient.

Preferably, the sulfur is employed in very small amount (From about 0.5 to about 3.0 part by weight for every 100 parts by weight of elastomers is suitable with 1.0 to 3.0 part preferred for tires, which amount would not be sufficient for vulcanization in the absence of peroxide and accelerator.

The mixture includes, in addition to the elastomers and the vulcanization system, also the customary ingredients such as antioxidant, extender or plasticizing oil, fillers (carbon black, silica, titanium and zinc oxides), activators, retarders, in proportions similar to those found in sidewall rubbers, depending on the properties desired. Thus, the mixtures contain from about 30 to about 65 parts by weight of carbon black per 100 parts by weight of total elastomer.

The vulcanization by the peroxides of sidewall blends having a base of elastomers of the ethylene-propylene type associated with diene elastomers along with the triazine compound of structure (I) surprisingly results in a number of advantages over the sulfur-vulcanization mixtures, namely:

1. Improvement in the resistance to ozone for an equal amount of ethylene-propylene elastomer. This advantage is the greater the more ethylene-propylenediene terpolymer is used and the higher its average molecular weight.

2. Improvement of the adherence to conventional rubber blends after vulcanization. The sidewall rubber adheres better to the carcass and, therefore, without risk of internal separation in the sidewall, one can use more elastomer of ethylene-propylene type and therefore enjoy better protection against ozone.

3. Improvement in the resistance to fatigue, particularly due to flexure.

The foregoing peroxide/sulfur cured blend of diene and EPDM is the most preferred form of polymer composition and curative. However, it is to be noted that the triazine of structure (I) is useful with conventional sulfur vulcanizing systems as have been commonly used with diene elastomer rubber carcassed tires. The general term "carcass" is used here as generally indicating all portions of the body of a bias or radial ply tire. Used as such, the carcass is composed of many, many different layers of elastomer. Some of the elastomer layers include fabric, or cords or other types of reinforcements incorporated within the layer. Some of the many components of a tire carcass are mentioned by way of example only. The crown or tread area of the tire overlays a crown reinforcement area in which the primary belts are imbedded which adds stability to the structure. Under the belts are the fabric reinforced innerplies which may be radially oriented or on a bias forming the body of the tire. Inward, from the carcass reinforcements, is the rubber inner liner layer. Now moving to the sidewall area, the sidewall may be formed of many layers but typically four layers are utilized moving from the crown down through the shoulder of the tire and eventually ending in the area of the bead. A radially inward first layer normally extends in varying thickness from the crown or tread area all the way down to near the bead reinforcement area. Radially outward from that innermost layer are layers which may include a white sidewall portion with black outermost layers lying on either side of the whitewall composition. It is these outermost sidewall layers in which the elastomer composition of this invention utilizing triazine of structure (I) is found to be most useful. The outermost sidewall layers are constantly exposed to the rigors of the environment and encounter millions of flex cycles during the life of a tire. It is highly desirable for these outermost sidewall layers to maintain good physical properties as well as an aesthetically correct appearance. When a black sidewall tire construction is being utilized, those outward layers are all black, the carbon black reinforced and it is highly desirable for those layers to maintain a jet black, shiny surface throughout the life of the tire If a white sidewall composition is included in the outermost sidewall, this it is of course desirable that the white sidewall portion remain white and not turn yellow or brown upon aging. It is well known that when using normal quantities such as 2-8 parts per 100 of rubber hydrocarbon of conventional paraphenylenediamine antiozonants, the white sidewall areas of a tire and even the black sidewalls undergo an aesthetically undesirable darkening with age and exposure to outdoor environmental conditions. The use of the triazine compounds of the invention has been shown to minimize the development of this undesirable discoloration in both white and black sidewall type elastomer compositions. The most preferred composition includes a base composition of diene based unsaturated elastomers as well as an EPDM elastomer. Such a combination withstands the ozone of the atmosphere for prolonged service life of the tire carcass area. This is particularly important in such applications as over-the-road truck tires where the tire carcass may be retreaded four, five or six times during its life, and the carcass may be required to go up to 1,000,000 miles of trouble free service.

The novel compounds of the invention may be used in combination with other antiozonants and less preferably with microcrystalline waxes as are commonly used to protect against static ozone attack. The other antiozonants which may be utilized include any of the commonly recognized paraphenylenediamine class of materials: N-phenyl-N'-(1,3-dimethylbutyl)-p-phenylenediamine; N-phenyl-N'-isopropyl-p-phenylenediamine; N-phenyl-N'-(1-methylheptyl)-p-phenylenediamine; N-phenyl-N'-cyclohexyl-p-phenylenediamine; mixed diarylp-phenylenediamines; N,N'-diphenyl-p-phenylenediamine: N,N'-di-beta-naphthyl-p-phenylenediamine; N,N'-bis(1,4-dimethylpentyl)-p-phenylenediamine; N,N'-bis(1-ethyl-3-methylpentyl)-p-phenylenediamine; N,N'-bis(1-methylheptyl)-p-phenylenediamine; N-phenyl-N'-p-toluenesulfonylp-phenylenediamine; N-phenyl-N'-alkyl-p-phenylenediamine; 6-ethoxy-1,2-dihydro-2,2,4-trimethylquinoline; and nickel dibutyl dithiocarbamate.

A most preferred antiozonant to be used in combination with the novel triazine compounds of the invention is N-phenyl-N'-(1,3-dimethylbutyl)-p-phenylenediamine.

The novel compounds of the invention may be added to an unsaturated polymer at a level of from 0.1 to about 10 parts by weight per hundred parts by weight of rubber hydrocarbon (hereinafter PHR). For these purposes the polymer is assumed to be a natural or synthetic rubber. A more preferred addition level is about 1 to about 8 parts PHR. The most preferred level is from about 2 to about 6 parts PHR. When the triazine compounds of the invention are used in combination with other antiozonants such as the paraphenylenediamine class of materials, they may be added in a blend which totals to the ranges set forth above, although higher cumulative levels than the preferred ranges indicated above may be ideal when these blends are employed. The compounds of the invention may be blended with the other antiozonants at ratios ranging from 1:3 to 3:1. More preferred is a ratio range of 2:3 to 3:2. These ratios are meant to indicate the percentages are 40:60 to 60:40 where in all cases the triazine compounds of the invention are the first number of each ratio. The most preferred is about 50:50. It should be noted that in certain applications and with certain other antiozonants, the PHR ranges of antiozonant listed above may be varied in order to obtain the optimal protection. Reasonable experimentation must be undertaken in order to optimize the ratios and overall levels of the blend when the triazine compounds of the invention are blended with other conventional antioxidants and antiozonants.

The novel triazine compounds of the invention may be synthesized by a suitable synthesis route. The following synthesis examples are provided to illustrate a currently preferred method of manufacturing certain of the class of triazine compounds (I) of the invention.

SYNTHESIS OF TRIAZINE COMPOUNDS

EXAMPLE 1:
2,4,6-tris(N-1,4-dimethylpentyl-p-phenylene diamino)-1,3,5-triazine In a 3-liter, four-necked, round-bottomed flask equipped with a thermometer, a mechanical stirrer, a condenser, and a dropping funnel was placed 1500 ml of isopropanol. The ispropanol was cooled to −10° C. and 184.4 grams (1 mole) of cyanuric chloride was added. To this stirred suspension was added 680 grams (3.3 moles) of 4-amino-N-(1,4 dimethylpentyl)aniline dropwise over 1 hour period keeping the temperature between −10° and −5° C. Over 1 hour the reaction mixture was warmed to 30° C. then held for 16 hours at 30° C. The reaction mixture was refluxed for 1 hour at about 80° C. The reaction was followed by high pressure liquid chromatograph by observing the disappearance of the starting amine, and the conversion of the intermediate mono- and bis- substituted compounds to the final tris-substituted product. After cooling to 60° C. 240 grams (3 moles) of 50 percent sodium hydroxide solution was added dropwise over 1 hour period. The sodium chloride was removed by filtration at 40° C. The filtrate was cooled to 10° C. and the solvent was decanted off. The oily lower layer was extracted with water at 60° C. then crystallized from fresh isopropanol. The title compound was recrystallized from hexane and it melted at 128°-132° C. The yield was 78.1 percent. The infrared spectrum was consistent with the structure. Relative area HPLC analysis of the product showed it to be 95.8 percent pure.

EXAMPLE 2:
2,4,6-tris(N-isopropyl-p-phenylenediamino)1,3,5-triazine

In a 2-liter, four-necked, round-bottomed flask equipped with a thermometer, a mechanical stirrer, a condenser, and a dropping funnel was placed 650 ml. of isopropanol. The isopropanol was cooled to −5° C. and 36.8 grams (.2 mole) of cyanuric chloride was added. To this stirred suspension was added a solution of 90 grams (0.6 mole) of 4-amino-N-isopropylaniline in 100 ml. of isopropanol dropwise over 1 hour period keeping the temperature between −5 and 0° C. Over ½ hour the reaction mixture was warmed to 30° C. then refluxed for 2 hours. The reaction was followed by high pressure liquid chromatography by observing the disappearance of the starting amine, and the conversion of the intermediate mono- and bis-substituted compounds to the final tris-substituted product. The reaction mixture was cooled, and allowed to stand overnight. The amine hydrochloride salt was neutralized by adding 96 grams (0.6 mole) of 25 percent sodium hydroxide solution over ½ hour period, and then refluxing the mixture for ½ hour. The title compound precipitated upon cooling and was isolated by filtration, washed with isopropanol and hot water (60° C.), M.P. 196°-198° C. The yield was 75.2 percent. The infrared spectrum was consistent with the structure. Relative area HPLC analysis of the product showed it to be 95.3 percent pure.

EXAMPLE 3:
2,4,6-tris(N-cyclohexyl-p-phenylenediamino)-1,3,5-triazine

The procedure of Example 2 was repeated except on a 0.1 molar scale with 4-amino-N-cyclohexylaniline used to produce the title compound, M.P. 215°-217° C. The yield was 89.9 percent. The infrared spectrum was consistent with the structure. Relative area HPLC analysis of the product showed it to be 90.1 percent pure.

EXAMPLE 4:
2,4,6-tris(N-sec-butyl-p-phenylenediamino)-1,3,5-triazine

The procedure of Example 2 was repeated except that 4-amino-N-sec-butylaniline was used to produce the title compound, M.P. 167°-169° C. The yield was 90.8 percent. The infrared spectrum was consistent with the structure. Relative area HPLC analysis of the product showed it to be 94.6 percent pure.

EXAMPLE 5:
2,4,6-tris(N-1,3-dimethylbutyl-p-phenylene diamino)-1,3,5-trazine In a 3-liter, four-necked, round-bottomed flask equipped with a thermometer, a mechanical stirrer, a condenser, and a powder funnel was placed a solution of 316.8 grams (1.65 moles) of 4-amino-N-(1,3 dimethylbutyl)aniline in 1500 ml of isopropanol. The temperature of the solution was adjusted to 30° C. and 92.2 grams (0.5 mole) of cyanuric chloride was added over ½ hour period keeping the temperature between 30° to 40° C. The reaction mixture was refluxed for 1-½ hours. The reaction was followed by high pressure liquid chromatography by observing the disappearance of the starting amine, and the conversion of the intermediate mono- and bis-substituted compounds to the final tris-substituted product. After cooling the reaction mixture to 60° C. 120 grams (1.5 moles) of 50 percent sodium hydroxide solution was added dropwise over 1 hour period. The sodium chloride was removed by filtration at 40° C. The filtrate was charged back to the reaction flask, and 250 ml of water was added dropwise. The title compound precipitated, and was removed by filtration, M.P. 124°-127° C. The yield was 82.6 percent. The infrared spectrum was consistent with the structure. Relative area HPLC analysis of the product showed it to be 95.3 percent pure.

EXAMPLE 6:
2,4,6-tris(N-1-methylheptyl-p-phenylenediamino)-1,3,5-triazine

The procedure of Example 5 was repeated except on a 0.225 molar scale with 4-amino-N-(1-methylheptyl)aniline used to produce the title compound. After recrystallization from a 28 percent toluene hexane mixture the melting point of the product was 87°-90° C. The infrared spectrum was consistent with the structure, and the relative area HPLC analysis of the product showed it to be 90.7 percent pure.

EXAMPLE 7:
2,4,6-tris(N-2,4-di-tert-butylcyclohexyl-p-phenylenediamino)-1,3,5-triazine The procedure of Example 5 was repeated except on a 0.25 molar scale with 4-amino-N-(2,4-di-t-butylcyclohexyl)aniline used to produce the title compound, M.P. 147°-152° C. The yield was 85.7 percent. The infrared spectrum was consistent with the structure.

EXAMPLE 8:
2,4,6-tris(N-2-sec-butylcyclohexyl-p-phenylenediamino)-1,3,5-triazine The procedure of Example 5 was repeated except on a 0.25 molar scale with 4-amino-N-(2-sec-butylcyclohexyl)-aniline used to produce the title compound. The product didn't crystallize, and was isolated as a pot residue, M.P. 122°-130° C. The yield was 95.8 percent. The infrared spectrum was consistent with the structure, and the relative area HPLC analysis of the product showed it to be 86.6 percent pure.

ANTIOZONANT UTILITY EXAMPLES 9-24

The N-alkylarylenediamino triazine compounds of the invention function as outstanding antiozonants in rubber polymers with no migratory staining tendency evident at this time. The following examples demonstrate their utility in a variety of ozone and color stability test regimes. All tests utilize the triazines in vulcanized rubber compounds as are typical in the industry. The following test formulation is a typical rubber compound.

| TEST FORMULATION | |
|---|---|
| | Parts by Weight |
| Natural Rubber (SMR5CV) | 50.0 |
| Polybutadiene (cis 1,4 BR) | 50.0 |
| Carbon Black (N-326) | 50.0 |
| Zinc Oxide | 3.0 |
| Microcrystalline Wax | 1.5 |
| Stearic Acid | 1.0 |
| Aromatic Oil | 5.0 |
| Benzothiazole Sulfenamide | 1.0 |
| Sulfur | 2.0 |
| Antiozonant - Variable | Variable |

| TABLE OF ANTIOZONANTS | |
|---|---|
| Comparative A | N-phenyl-N'-(1,3-dimethylbutyl)-p-phenylenediamine (commercially available as Flexzone TM 7F from Uniroyal Chemical Company) |
| Comparative B | mixed diaryl -p-phenylenediamine (commercially available as Novazone TM AS from Uniroyal Chemical Company) |
| Example 1 | 2,4,6-tris(N-1,4-dimethylpentyl-p-phenylenediamino)-1,3,5-triazine |

The foregoing test formulation was used for all test samples unless otherwise noted. The formulation is an approximation of a typical tire sidewall compound. The identity and level of the antiozonant are the variables to be evaluated in the subsequent examples.

The test formulation was utilized to make uncured test sheets by preblending the natural rubber and polybutadiene. Once blending was accomplished, all other ingredients except the sulfur and benzothiazole sulfenamide were added to form a nonproductive compound and in a subsequent mixing step, the foregoing ingredients were added. Tests sheets for the subsequent testing were cured in a platen press between heated plates for a time sufficient to achieve full cure. For the purposes of testing, a fifteen minute cure at 160° C. was normally utilized. The exact sample configuration of the test specimens for the ozone testing varies by the description of the ASTM method utilized. Reference is made to the ASTM test methods and such methods are incorporated herein by reference to abbreviate the required descriptive information regarding specimen preparation, test methods and test results.

OZONE TEST RESULTS

Ozone testing was conducted utilizing the standard test method of ASTM D1149-81 which is titled Rubber Deterioration - Surface Zone Cracking in a Chamber (Flat Specimen). This method covers the estimation of the resistance of vulcanized rubber to cracking when exposed to an atmosphere containing ozone. Rubber specimens are kept under a surface tensile strain and the ozone content in the test chamber is maintained at a 50 part per hundred million level in a 100° F. (38° C.) test chamber. A common designation for this test is the bent loop test method since the test specimen is placed under strain by having it clamped in a looped configuration in which varying degrees of strain and elongation result. This bent loop configuration is an extremely severe test configuration in which failure can be expected in a relatively few hours given the high temperature and high ozone atmosphere in which the test samples are placed.

TABLE I

STATIC OZONE TESTING
(Results in Hours)

| | EXAMPLE # | | |
|---|---|---|---|
| | 9 | 10 | 11 |
| | | ANTIOZONANT, 4 PHR | |
| OZONE BOX - STATIC TEST | Blank | Comparative A | Example 1 |
| Unaged | | | |
| No Cracks | — | — | 1128 |
| Cracked | 6 | 600 | — |
| 6 Months Aged | | | |
| No Cracks | — | — | 1080 |
| Cracked | 8 | 24 | — |
| 12 Month Aged | | | |
| No Cracks | — | — | 1040 |
| Cracked | 17 | 40 | — |

The prepared specimens were aged unstressed at room temperature at six months and twelve months and tested. Accordingly, three sets of test data are presented: unaged, six month and twelve month aged. The Example 9 column headed by the term blank denotes a formulation which contains no antiozonant protection. That unprotected sample broke in between six and seventeen hours of exposure depending upon the degree of aging which the specimen underwent prior to ozone exposure. Example 10 with Comparative A is the result of the conventional paraphenylenediamine (Flexzone 7F) added at four parts PHR and it cracked between 600 and as low as 24 hours of exposure. In Example 11, the rubber formulation protected by the substituted triazine of the invention shown in Example 1 survived between 1040 and 1128 hours for the various unaged and aged samples. It is clear from these results that the ozone protection afforded by the compounds of this invention are outstanding compared to the conventional antiozonants which are well known in the rubber field.

Table II shows the data for static ozone testing conducted in a similar manner to the testing shown in Table I. Test specimens dumbells, 3mm by 50 mm were stretched 20% on specially designed racks and the degree of cracking was periodically recorded. Under this method, the test sample is subjected to the ozone atmosphere of 50 parts per hundred million at 100° F. while under 20% elongation or extension. This additional degree of strain is a added characteristic of the sample preparation that is different than the test conducted as shown in Table I. All other details with respect to the test method are similar to those previously reported for the Table I results.

TABLE II

OZONE EXPOSURE 20% EXTENSION
(Results in Hours)

| | EXAMPLE # | | |
|---|---|---|---|
| | 12 | 13 | 14 |
| | | ANTIOZONANT, 4 PHR | |
| | BLANK | COMPARATIVE A | EXAMPLE 1 |
| Unaged | | | |
| No Cracks | — | 600* | 1128 |
| Cracked | 552 | — | — |
| 6 Months Aged | | | |
| No Cracks | — | — | 1080 |
| Cracked | 8 | 24 | — |
| 12 Month Aged | | | |
| No Cracks | — | — | 1040 |
| Cracked | 12 | 56 | — |

*Very slight cracking is visible

The unprotected blank test specimens of Example 12 survived between 8 and 552 hours depending on how long the sample was aged. The Comparative A composition when in an unaged condition at 600 hours showed very slight cracking. The six month and twelve month aged Example 13 showed cracking of the sample in between 56 and 24 hours. The compounds of this invention shown as example #14 again showed very dramatic improvements over the prior art antiozonant in providing protection which exceeded 1000 hours at these test conditions. This again demonstrates the superiority of the N-alkyl arylenediamino triazines of this invention over the conventionally used antiozonant of the paraphenylenediamine class.

Rubber articles must be protected against ozone when they are subjected to such exposure on outdoor weathering. One of the most difficult applications is on a tire where the vehicle remains outdoors and in ozone bearing atmosphere for an indefinite period of time. The true service conditions under which tires operate are not well duplicated by either static ozone tests such as those described in Table I and II nor are they well duplicated using dynamic test procedures such as De-Mattia Flex Testing. In an effort to simulate a typical tire surface condition the following test method is utilized. In the testing scheme, samples are mounted in southern facing test fixtures outdoors, exposed to the full outdoor environmental conditions as are present in Naugatuck, Conn. The samples are continuously flexed for 8 hours over approximately a 78° angle. After this flexing period the sample is then relaxed and remains in that relaxed, static condition for 16 hours. This protocol is repeated day after day until the deterioration as evidenced by the appearance and growth of cracks on the sample surface is observed and recorded. This intermittent flex/relaxation test is felt to correlate well with the actual conditions under which a tire operates. That is, the tire is driven for a number of hours in which it is cycled to similar extensions as are accomplished during the flexing portion of the test. Then the tire sits for a prolonged period of time in a static condition which is reproduced in the 16 hour static portion of the cycle. The test results are expressed in kilocycles. During the flexing portion of the test, the samples are flexed through a 78° angle at about 8.5 kilocycles per hour.

TABLE III

DYNAMIC OZONE TESTING
(Results in Kilocycles)

| 8 HOUR FLEX/<br>16 HOUR STATIC<br>RESULTS IN KILOCYCLES | EXAMPLE # | | |
| --- | --- | --- | --- |
| | 15 | 16 | 17 |
| | | ANTIOZONANT, 4 PHR | |
| | Blank | Comparative<br>A | Example 1 |
| Unaged | | | |
| No Cracks | — | — | — |
| Cracked | 1694 | 8264 | 8584 |
| ¹6 Months Aged | | | |
| No Cracks | — | 13896* | 16588* |
| Cracked | 2969 | — | — |
| ¹12 Month Aged | | | |
| No Cracks | — | 7655* | 7655* |
| Cracked | 1165 | — | — |

¹Test ongoing
*Very, very slight cracking is visible
Note:
No microcrystalline wax in 15, 16, 17.

This dynamic flexing test uses rectangular specimens 12 mm by 76 mm with a 3 mm radius circular groove across the center of the specimen.

It is apparent from the results, that Example 15 which contained no antiozonant survived less than 3000 kilocycles under this test. Examples 16 and 17, which are protected by the paraphenylenediamine of the prior art and a triazine of this invention, respectively, exhibited very significant improvements in the ability to withstand the outdoor aging. The triazine compound of the invention protected the sample of Example 17 with very nearly the same result as the paraphenylenediamine of Comparative A, which is generally considered to be one of the best antiozonants available for dynamic applicants.

ANTIOZONANT BLENDING—EXAMPLES 18-21

The triazine compounds of the invention, when compared to N-phenyl-N'-(1,3-dimethylbutyl)-p-phenylenediamine (Comparative A - Flexzone 7F) generally exhibit much better protection under static conditions and slightly poorer protection under severe dynamic conditions as judged by various laboratory test methods. However, it has been quite unexpectedly and surprisingly found that the dynamic protection properties may be greatly improved by blending the triazine compounds with conventional p-phenylene diamines. This is accomplished without sacrificing static condition ozone protection. Examples 18-21 below demonstrate this synergistic effect.

In Examples 18 and 19, the antiozonant of Example 1 was blended with two conventional antiozonants to evaluate the cumulative effect under both static and dynamic ozone testing conditions. The results were compared to unblended controls 20 and 21. The rubber formulation utilized was the same as the Test Formulation previously used in all test work except that the microcrystalline wax was deleted to assure that the antiozonant effect of the wax was not present to affect the results.

The Outdoor Dynamic Ozone test was conducted in a similar manner to the 8 hour flex/16 hour static test for Examples 12-14 of Table III except that the flexing at 8.5 kilocycles per hour is run continuously. There is no relaxation period. The rest was ongoing, and therefore, no samples have yet reached the point of final cracking (failure).

The Ozone Box Static Test was run as described for Examples 9-11.

TABLE IV

ANTIOZONANT BLEND TESTING

| | EXAMPLE # | | | |
| --- | --- | --- | --- | --- |
| | 18 | 19 | 20 | 21 |
| ANTIOZONANT, PHR | | | | |
| Example 1 | 2.5 | 3.0 | — | 4.0 |
| Comparative A | — | 1.0 | 4.0 | — |
| Comparative B | 1.5 | — | — | — |
| OZONE BOX STATIC TEST (in hours) | | | | |
| No Cracks | 1016 | 1016 | — | 1016 |
| *VVS | — | — | — | — |
| Cracked | — | — | 216 | — |
| OUTDOOR DYNAMIC TEST Continuous Flexing (in kilocycles) | | | | |
| No Cracks | 14583** | 14583** | 14583** | — |
| *VVS | — | — | — | 4231 |
| Cracked | — | — | — | — |

*VVS — First appearance of very, very slight cracks
**Test still underway last reading at 14583 kilocycles.

The results shown in Table IV for the Ozone Box Static Test show that Comparative A (Flexzone 7F) cracks after 216 hours (Example 20) while the compound of Example 1, used in Examples 18, 19, 21 alone or in combination with Comparative A or B afforded excellent protection as indicated by the fact that no cracks were evident after 1016 hours.

The Outdoor Dynamic Test results of Examples 18-20 show that the blends of Example 1 with Comparative A and B showed excellent protection under dynamic conditions. The blends of Examples 18 and 19 unexpectedly improved the Dynamic Ozone resistance compared to Example 21 which used the compound of Example 1 alone.

NON-STAINING CHARACTERISTICS - EXAMPLES 22-24

Samples specimens were prepared using the test formulation set forth previously but without wax. The test formulation was compounded, mixed and cured into flat test sheets for subsequent analysis of discoloration and staining characteristics. The specific testing was conducted in accordance ASTM-D925-83 Method C. The Method C judges the degree of staining tendency of material by determining the amount of discoloration that occurs from the substrate material through a white lacquer coating which has been placed on the test sample. The test formulation previously set forth for all test samples of the invention was utilized. Once the test specimen was mixed and cured, it was coated with a veneer of white lacquer in accordance with the ASTM-D925 procedure. It was then exposed to a sunlamp light source in a suitable test chamber for a specified period of time. The Hunter Lab ™ Colorimeter test apparatus was utilized to objectively determine the change in the color of the white lacquer during the four-hour exposure to the sun lamp. ASTM D2244-79 titled "Color Differences of Opaque Materials", reports a number of characteristics by the standard difference letters a, b, and L. Since the staining characteristics of normal antiozonants are very extreme, the L color scale is reported below. The L color scale is a scale from 0 to 100 with a 0 value being totally black and a 100 value being pure white. Therefore the higher the L value, the whiter the sample. The Test formulation of Example 22 was prepared as a blank which contain no antiozonant. Example 24 contains the antiozonant of the invention described in Example 1, 2,4,6-tris(N-1,4-dimethylpentyl-p-phenylenediamino)-1,3,-5-triazine.

Example 23 uses the Comparative A material which is N-phenyl-N'-(1,3-dimethylbutyl)-p-phenylenediamine (Flexzone 7F, available from Uniroyal Chemical Company, Inc.). The test results of the three samples are presented below in Table V showing the Hunter "L" value after four hours of exposure.

TABLE V

| HUNTER "L" COLOR RESULTS EXAMPLE | | |
|---|---|---|
| 22 | 23 | 24 |
| | ANTIOZONANT | |
| blank | Comparative A | Example 1 |
| 87.9 | 32.6 | 81.5 |

The results shown above clearly show that the conventional paraphenylenediamine material of Example 23 shows significant staining (32.6) after 4 hours of exposure. But by contrast the test formula containing the compound of the invention of Example 1 had a color value of 81.5 which is very close to 87.9 value reported for the blank of Example 22. Thus, the compound of the invention is shown to have minimal diffusion staining which is an extremely unusual result for stabilizer of the amine class. Thus, the compounds of the invention can be advantageously utilized as antiozonants without the normal accompanying problems of diffusion staining and severe discoloration such as that shown in Comparative A results above. This class of materials could be described as non-staining antiozonants.

The compounds of the invention may be used to good advantage with antioxidants and antiozonants of the prior art in blends to enhance particular properties. While the substituted triazine compounds of the invention have herein described only as antiozonants, it is clear that the materials may also function as antioxidants for rubber, thus providing protection against oxidative degradation as well as ozone protection. It is noted that when used as an antioxidant, the levels are typically much lower per hundred parts of rubber hydrocarbon than when antiozonant protection is required.

Unsaturated polymers may be optionally protected against both oxidative and ozone degradation by blending the triazine compounds of the invention with conventional antioxidants. Many classes of phenolics, amines, etc. function as antioxidants. The Index of Commercial Antioxidants and Antiozonants, 3rd Edition published by The Goodyear Tire and Rubber Company lists materials commonly viewed as materials having antioxidant properties, and is incorporated herein by reference. Representative classes of such antioxidant materials are sterically hindered phenols, alkyl-substituted diphenylamines, aryl-substituted diphenylamines, aralkylsubstituted diphenylamines, naphthylamines, reaction products of a diarylamine and a ketone, mono-phenols, bisphenols, polyphenols, hydroquinone derivatives, and polymerized quinolines. The antioxidant system may contain one or more of these materials. Optimal levels of addition (PHR) for the antioxidants can be easily determined through routine experimentation and may vary widely depending upon the end use application.

The 2,4,6-tris(N-alkyl-p-phenylenediamino)-1,3,5-triazines can be most advantageously used in a tire as a component of any or all of the thermosetting rubber-containing portions of the tire. These include the tread, sidewall and carcass portions of a truck, passenger or off-road vehicle tire which also contain many different reinforcing layers therein. These components typically contain more than one thermosetting rubber polymer in a blend which must be protected from ozone degration, as well as oxidative attack.

Methods of incorporating these compounds into the tire are conventional and well known. These compounds improve the scorch safety of the rubber stock in which they are incorporated compared to conventional paraphenylenediamines.

TIRE SIDEWALL COMPOSITIONS—EXAMPLES 25-33

The following examples illustrate the preferred utility of the triazines in pneumatic tire exterior sidewall compounds containing blends of highly unsaturated rubber as well as EPDM which has lesser unsaturation.

Examples 25, 26 and 27 are comparative examples, not within the scope of the invention. Example 25 does not contain either the essential triazine component (I) of the invention or EPDM. Examples 26 and 27 have no triazine. These controls show cracking in the 72 hour ozone belt test (ASTM D-3395B-82) which is an extremely severe dynamic ozone test method in which the compound samples are vulcanized onto a fabric belt.

TABLE VI

| | EXAMPLE # | | | | | | | | |
|---|---|---|---|---|---|---|---|---|---|
| | 25 | 26 | 27 | 28 | 29 | 30 | 31 | 32 | 33 |
| Natural Rubber (SMR 5CV) | 60.00 | 60.00 | 60.00 | 60.00 | 60.00 | 60.00 | 60.00 | 60.00 | 60.00 |
| Polybutadiene (Cis 1,4-BR) | 40.00 | 30.00 | 10.00 | 10.00 | 30.00 | 25.00 | 25.00 | 25.00 | 20.00 |
| EPDM[1] | — | 10.00 | 30.00 | 30.00 | 10.00 | 15.00 | 15.00 | 15.00 | 20.00 |
| Carbon Black (N-326) | 45.00 | 45.00 | 45.00 | 45.00 | 45.00 | 45.00 | 45.00 | 45.00 | 45.00 |
| Naphthenic oil (Circosol 4240) | 12.00 | 12.00 | 22.50 | 22.50 | 12.00 | 12.00 | 12.00 | 12.00 | 12.00 |
| Zinc Oxide | 5.00 | 5.00 | 5.00 | 5.00 | 5.00 | 5.00 | 5.00 | 5.00 | 5.00 |
| Stearic Acid | 1.50 | 1.50 | 1.50 | 1.50 | 1.50 | 1.50 | 1.50 | 1.50 | 1.50 |
| Triazine Antiozonant[2] | — | — | — | 2.00 | 2.00 | 2.00 | 3.50 | 2.50 | 2.00 |
| Antiozonant[3] | — | — | — | — | 1.50 | 1.50 | 1.50 | 1.50 | 1.50 |
| 2(Morpholinothio)benzothiazole | 0.70 | 0.70 | 0.70 | 0.70 | 0.70 | 0.70 | 0.70 | 0.70 | 0.70 |
| Sulfur (80% oiled) | 2.25 | 2.25 | 2.25 | 2.25 | 2.25 | 2.25 | 2.25 | 2.25 | 2.25 |
| Mooney Scorch @ 132° C. (270° F.) ASTM D-1646 | | | | | | | | | |
| Scorch Time (minutes) | 24.00 | 24.00 | 22.50 | 16.25 | 20.80 | 20.71 | 20.56 | 20.29 | 19.19 |
| Cure Rate (minutes) | 14.25 | 24.25 | 10.00 | 6.45 | 13.90 | 12.76 | 10.67 | 10.75 | 10.76 |
| Monsanto Fatigue Flex ASTM D-4482-85 KC to Failure | 73.90 | 67.60 | 134.10 | 117.80 | 84.30 | 99.40 | 84.00 | 75.10 | 89.00 |

TABLE VI-continued

| | EXAMPLE # | | | | | | | | |
|---|---|---|---|---|---|---|---|---|---|
| | 25 | 26 | 27 | 28 | 29 | 30 | 31 | 32 | 33 |
| Cured 18 Minutes @ 150° F. (aged 70 hours @ 100° C.) DeMattia Flex Cracking ASTM D-430-73 Method B | NR[4] | NR | NR | NR | 1236 | 1084 | 898 | 730 | 1354 |
| Ozone Exposure ASTM D-1149-81 Bent Loop @ 50 pphm/38° C. (hours) | | | | | | | | | |
| OK | NR | NR | NR | NR | | | 1080 | 1080 | 1080 |
| VVS | | | | | 4 | 8 | | | |
| VS | | | | | 8 | — | | | |
| S | | | | | — | 96 | | | |
| C | | | | | 96 | 456 | | | |
| Dynamic Ozone Belt at 50 pphm ASTM D-3395B-82 @ 38° C., 72 continuous hours Crack Rating | C | C | VVS | OK | NR | NR | NR | NR | NR |

[1] Ethylene-propylene-5-ethylidene-2-norbornene terpolymer: E/P wt. ratio = 66/34; diene wt. % = 82; IV = 26 dl/g (decalin @ 135° C.); Mooney Viscosity (ML 1 + 4 @ 100° C.) = 65 on 75 phr oil extended polymer. All oil reported in naphthenic oil line below.
[2] 2,4,6-tris(N-1,4-dimethylpentyl-p-phenylenediamino)-1,3,5-triazine (See Example 1 for synthesis).
[3] Mixed diaryl-p-phenylenediamine (commercially available as Novazone TM AS from Uniroyal Chemical Company, Inc.
[4] NR — not run.
[5] OK — no cracks; VS — very slight cracks; VVS — very, very slight cracks; S — slight cracks and C — cracked.

The belt is run over a set of pulleys to induce a surface strain in an ozone chamber at 50 parts per hundred million of ozone at 100° F.

Examples 25 and 26 cracked during the ozone belt exposure while Example 27 showed an improved result (very, very slight cracking) due to the presence of the EPDM.

Example 28 dramatically illustrates the advancement in the art of rubber compounding. This compound, having both the essential triazine and the EPDM survived the severe dynamic ozone test with no cracking whatsoever.

Examples 29-33 illustrate the importance of the levels of addition of the essential EPDM and triazine components of the invention. Without being held to the scientific validity of the explanation, it is currently felt that optional protection can be obtained by having adequately high levels of either EPDM or the triazine compound. It is not felt to be necessary to have high levels of both to obtain exceptional dynamic ozone and fatigue properties. However, it is to be noted that good to excellent ozone resistance can be obtained in the lower ranges of either critical component compared to other non-staining ozone protection methods.

The effect of progressively higher levels of the triazine compound (of Example 1) is shown by looking at the ozone exposure (bent loop test) results of Examples 29 and 30 (two parts of triazine compound) which show cracks developing during the test. While the higher addition levels of Examples 31 and 32 show no cracking through the 1080 hours of the test.

The positive effect of progressively higher levels of EPDM is shown by comparing Examples 29, 30 and 33 which have progressively more EPDM. The level of ozone protection goes up with the EPDM level. The essential triazine compound is present at a constant level in these three examples. Thus, it can be concluded that desirable properties can be obtained by varying the level of lesser unsaturation elastomer (i.e. EPDM) and triazine compound.

TABLE VII

| | EXAMPLE # | | | | | | | |
|---|---|---|---|---|---|---|---|---|
| | 34 | 35 | 36 | 37 | 37 | 39 | 40 | 41 |
| Natural Rubber (SMR 5CV) | 50.00 | 50.00 | 50.00 | 50.00 | 50.00 | 50.00 | 60.00 | 60.00 |
| Polybutadiene (PBD 1203) | 50.00 | 20.00 | 50.00 | 20.00 | 20.00 | 20.00 | — | — |
| EPDM[1] | — | 30.00 | — | 30.00 | 30.00 | 30.00 | 40.00 | 40.00 |
| Carbon Black (N-326) | 50.00 | 50.00 | 50.00 | 50.00 | 50.00 | 50.00 | 50.00 | 50.00 |
| Naphthenic oil (Circosol 4240) | 10.00 | 30.00 | 10.00 | 30.00 | 30.00 | 30.00 | 36.00 | 36.00 |
| Zinc Oxide | 5.00 | 5.00 | 5.00 | 5.00 | 5.00 | 5.00 | 5.00 | 5.00 |
| Stearic Acid | 1.50 | 1.50 | 1.50 | 1.50 | 1.50 | 1.50 | 1.50 | 1.50 |
| Triazine Antiozonant[2] | — | — | 4.00 | 4.00 | 2.00 | 2.00 | — | 4.00 |
| N-t-butyl-2-benzothiazole sulfenamide | 1.00 | 1.00 | 1.00 | 1.00 | 1.00 | 0.85 | 0.85 | 0.85 |
| Dicumyl Peroxide (60%) | — | — | — | — | — | 1.00 | 1.00 | 1.00 |
| Sulfur (80%) | 2.00 | 2.00 | 2.00 | 2.00 | 2.00 | 1.50 | 1.50 | 1.50 |
| Mooney Scorch @ 132° C. (270 F.) ASTM 1646 | | | | | | | | |
| Scorch Time (minutes) | 24.00 | 28.75 | 27.50 | 28.00 | 30.00 | 22.50 | 14.25 | 20.75 |
| Cure Rate (minutes) | 12.50 | 10.50 | 7.50 | 5.50 | 5.75 | 15.25 | 12.75 | 9.00 |
| Monsanto Fatigue Flex ASTM-D-4482-85 KC to Failure | | | | | | | | |
| Cured 18 Minutes @ 150° F. (aged 70 hours @ 100° C.) | 4.50 | 13.30 | 34.60 | 106.00 | 63.60 | 75.00 | 104.9 | 162.6 |
| Static Adhesion @100° C. | * | 24.6 | * | 25.4 | 26.4 | 22.7 | 19.9 | 14.5 |

TABLE VII-continued

| | EXAMPLE # | | | | | | | |
|---|---|---|---|---|---|---|---|---|
| | 34 | 35 | 36 | 37 | 37 | 39 | 40 | 41 |
| Adhesion, kN/m | *19.6 | 21.6 | * | 23.6 | 26.9 | *20.5 | 15.3 | 15.7 |

[1]See Footnote 1, Table VI.
[2]See Footnote 2, Table VI.
*Test sample slipped out of one of the grips.

EXAMPLES 34–41

Examples 34, 35, 36, and 40 are comparative examples not within the scope of this invention. 34, 35 and 40 have no triazine antiozonant and 34 and 36 have no EPDM (lesser unsaturation polymer). The Monsanto Fatigue Flex Results are very critical results which have a good correlation to tire carcass life properties. Example 37 shows a flex fatigue value of 106 versus the much lower values of comparatives 34, 35, 36 which are all missing at least one key component of the invention.

The advantages of utilizing the preferred peroxide/sulfur combination curing system is shown by comparing the flex fatigue results of comparative example 35 (13.3) versus 39 and 41 (75 and 162.6). The cure system selection is another important factor. Peroxide/sulfur combination curing improves the flex fatigue results.

The importance of the triazine antiozonant is shown by comparing the flex fatigue value of comparative Example 35 (13.3) versus Example 37 (106). Example 41 shows optimum flex fatigue results with high molecular weight EPDM, triazine antiozonant and peroxide/sulfur cure system.

In a tire a new compound is only useful if it has good adhesion to adjacent rubber layers of the tires. The static adhesion test results are consistently good for all stocks of the invention a value of 10 is generally considered fully adequate adhesion results. The adhesion of characteristics of each compound of the examples were evaluated for their adhesion to the standard tread test formulation shown below in Table VIII. The test compound was plied up against the standard tread formulation with a ply of RFL treated fabric on both sides to form a test pad. The pad was press cured 15 minutes @177° C. The cured pad was pulled in a Scott tester (or Instron) to yield the force necessary to cause the test compound to separate from the standard test tread formulation. Duplicate samples were tested and reported in Table VII in kilonewtons/meter.

TABLE VIII
STANDARD TREAD TEST FORMULATION FOR STATIC ADHESION TEST

| | |
|---|---|
| Styrene Butadiene Rubber (SVR-1500) | 55.0 |
| Polybutadiene (PBD 1203) | 25.0 |
| Natural Rubber (SMR 5CV) | 20.0 |
| Carbon Black (N-234) | 55.0 |
| Zinc Oxide | 3.0 |
| Microcrystalline Wax | 0.5 |
| N-phenyl-N'(1,3-dimethylbutyl)-p-phenylenediamine | 1.0 |
| Stearic Acid | 1.0 |
| Aromatic Oil | 20.0 |
| 2-(Morpholinothio)benzothiazole | 0.5 |
| Thiocarbamyl Sulfenamide | 0.5 |
| Sulfur | 2.0 |

In view of the many changes and modifications that may be made without departing from principles underlying the invention, reference should be made to the appended claims for an understanding of the scope of the protection afforded the invention.

What is claimed is:

1. A thermosetting composition comprising an admixture of:
   (a) at least one highly unsaturated rubbery polymer;
   (b) at least one elastomer having lesser unsaturation than said highly unsaturated rubbery polymer;
   (c) a compound of structure (I):

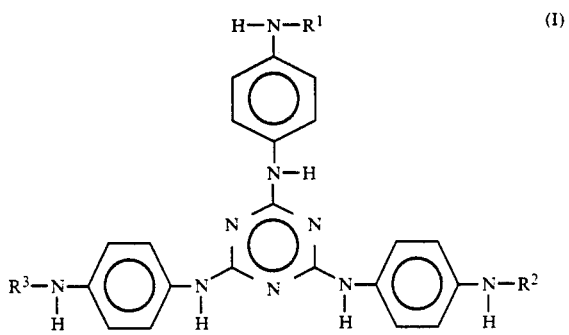

in which $R^1$, $R^2$ and $R^3$ are radicals independently selected from a $C_3$–$C_{18}$ branched or linear alkyl, or a $C_3$–$C_{12}$ cycloalkyl or a $C_3$–$C_{12}$ cycloalkyl substituted with one or more $C_1$–$C_{12}$ alkyl groups;
   (d) at least one sulfur-containing cure component selected from the group consisting of elemental sulfur and a sulfur donor accelerator compound; and
   (e) at least one organic peroxide curative.

2. A composition according to claim 1 wherein said sulfur donor accelerator is selected from the group consisting of 2-(4-morpholinyldithio)benzothiazole, tetramethylthiuram disulfide, tetraethylthiuram disulfide, dipentamethylene thiuram hexasulfide, and N,N'-caprolactam disulfide.

3. A composition according to claim 1 further comprising a sulfur cure accelerator selected from the group consisting of thioureas, guanidine derivatives, zanthantes, dithiocarbamates, thiuramsulfides, thiazoles and sulfenamides.

4. A composition according to claim 2 wherein said sulfur donor accelerator is a thiazole or a sulfenamide.

5. A composition according to claim 1 wherein said peroxide is selected from the group consisting of benzoyl peroxide, dibenzoyl peroxide, 1,3-bis(t-butylperoxyisopropyl)benzene, dicetyl peroxide, butyl 4,4-bis(t-butylperoxy)valerate, p-chlorobenzoyl peroxide, cumene hydroperoxide, t-butyl cumyl peroxide, t-butyl perbenzoate, di-t-butyl peroxide, dicumyl peroxide, 2,5-dimethyl-2,5-di-t-butylperoxyhexane, 2,5-dimethyl-2,5-di-t-butyl-peroxyhex-3-yne, and 4-methyl-2,2-di-t-butylperoxypentane.

6. A tire having a tread portion and a sidewall portion, said tire comprising:
   a rubber carcass including a plurality of layers of thermosetting rubber polymers therein and a plurality of layers of reinforcing materials positioned within said carcass, at least one of said plurality of thermosetting rubber polymers being composed of at least one high unsaturated polymer blended with a polymer having lesser unsaturation to form a blend, said blend having dispersed therein an antidegradant composition of:

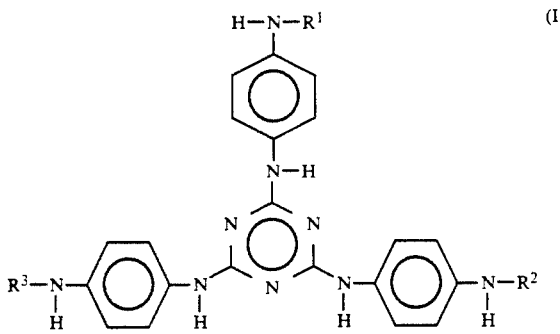

in which $R^1$, $R^2$ and $R^3$ are radicals independently selected from a $C_3$–$C_{18}$ branched or linear alkyl, or a $C_3$–$C_{12}$ cycloalkyl or a $C_3$–$C_{12}$ cycloalkyl substituted with one or more $C_1$–$C_{12}$ alkyl groups.

7. A tire according to claim 6 wherein said antidegradant composition further comprises an effective amount of a N-phenyl-N'-(1,3-dimethylbutyl)-p-phenylenediamine; N-phenyl-N'-isopropyl-p-phenylenediamine; N-phenyl-N'-(1,4-dimethylpentyl)-p-phenylenediamine; N-phenyl-N'-(1-methylheptyl)-p-phenylenediamine; N-phenyl-N'-cyclohexyl-p-phenylenediamine; mixed diarylp-phenylenediamines; N,N'-diphenyl-p-phenylenediamine; N,N'-di-beta-naphthyl-p-phenylenediamine; N,N'-bis(1,4-dimethylpentyl)-p-phenylenediamine; N,N'-bis(1-ethyl-3-methylpentyl)-p-phenylenediamine; N,N'-bis(1-methylheptyl)-p-phenylenediamine; N-phenyl-N'-p-toluenesulfonyl-p-phenylenediamine.

8. A tire according to claim 7 wherein said antidegradant composition further comprises:
an antioxidant system incorporated into said polymer, said antioxidant system having one or more materials selected from the group of materials exhibiting antioxidant properties consisting of sterically hindered phenols, alkyl-substituted diphenylamines, aryl-substituted diphenylamines, aralkyl-substituted diphenylamines, naphthylamines, reaction products of a diarylamine and a ketone, monophenols, bisphenols, polyphenols, hydroquinone derivatives, and polymerized quinolines.

9. A tire according to claim 6, wherein said sidewall portion of said rubber carcass includes in said plurality of thermosetting rubber polymers at least one highly unsaturated polymer having an iodine number of between about 100 and 400.

10. A tire according to claim 9, wherein said one highly unsaturated polymer is selected from the group consisting of natural rubber, cis-polyisoprene, polybutadiene and poly(styrene-butadiene).

11. A tire according to claim 10 further comprising an elastomer having lesser unsaturation than said highly unsaturated polymer, said elastomer being selected from the group consisting of EPDM, EPR, butyl rubber and halogenated butyl rubber.

12. A tire according to claim 10, wherein said antidegradant composition further comprises an effective amount of at least one paraphenylenediamine antiozonant.

13. A tire according to claim 12, wherein the amount of compound of structure (I) is between 0:1 to about 10 parts by weight per one hundred parts by weight of said thermosetting rubber, and the ratio of paraphenylenediamine antiozonant to the compound of structure (I) is from 1:3 to 3:1.

14. A tire according to claim 13, wherein said compound of structure (I) is added at levels of about 1 to about 6 parts by weight per one hundred parts of said thermosetting rubber polymers.

15. A tire according to claim 12, wherein said antidegradant composition is present at a level of 1 to 6 parts by weight per one hundred parts by weight of said thermosetting rubber polymers.

16. A tire according to claim 15, wherein said paraphenylenediamine and said compound of a structure (I) are present in said antidegradant composition in a ratio from 1:3 to 3:1.

17. A tire according to claim 6 wherein said elastomers having lesser unsaturation is an ethylene-propylene-diene rubber having an ethylene to propylene weight ratio of about 50:50 to about 75:25 and having about 2 to about 20 weight percent non-conjugated diene based on total weight of said EPDM rubber.

18. A tire according to claim 17 wherein said ethylene-propylene-diene rubber is an admixture with N-chlorothiosulfonamide.

19. A tire according to claim 18 wherein said non-conjugated diene in said ethylene-propylene-diene rubber is ethylidene norbornene at about 2 to about 20 weight percent of total ethylene-propylene-diene rubber.

20. A tire according to claim 17 wherein said ethylene-propylene-diene rubber is of high molecular weight and extended with between 50 and 150 parts by wight of oil per 100 parts of rubber.

* * * * *